US010165990B2

(12) United States Patent
Kim

(10) Patent No.: US 10,165,990 B2
(45) Date of Patent: Jan. 1, 2019

(54) INTRAORAL X-RAY DETECTOR

(71) Applicant: Rayence Co., Ltd., Gyeonggi-do (KR)

(72) Inventor: Jung Do Kim, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 221 days.

(21) Appl. No.: 15/108,327

(22) PCT Filed: Dec. 26, 2014

(86) PCT No.: PCT/KR2014/012903
§ 371 (c)(1),
(2) Date: Jun. 27, 2016

(87) PCT Pub. No.: WO2015/099487
PCT Pub. Date: Jul. 2, 2015

(65) Prior Publication Data
US 2016/0324491 A1 Nov. 10, 2016

(30) Foreign Application Priority Data

Dec. 27, 2013 (KR) .................. 10-2013-0165339
Dec. 1, 2014 (KR) .................. 10-2014-0169743
Dec. 1, 2014 (KR) .................. 10-2014-0169744

(51) Int. Cl.
*A61B 6/14* (2006.01)
*A61B 6/00* (2006.01)

(52) U.S. Cl.
CPC .............. *A61B 6/145* (2013.01); *A61B 6/425* (2013.01); *A61B 6/4452* (2013.01)

(58) Field of Classification Search
CPC .......... A61B 6/145; A61B 6/14; A61B 6/425; A61B 6/4452; A61B 6/4405
See application file for complete search history.

(56) References Cited

U.S. PATENT DOCUMENTS 6,030,119 A 2/2000 Tachibana et al.

FOREIGN PATENT DOCUMENTS

CN 202308475 U * 7/2012 ............. H01R 13/46
JP 10-277028 A 10/1998
(Continued)

OTHER PUBLICATIONS

Machine translation of KR 1998-017858 U published on Jul. 6, 1998.*

*Primary Examiner* — Chih-Cheng Kao
(74) *Attorney, Agent, or Firm* — IP Legal Services, LLC

(57) ABSTRACT

The present invention discloses a device for detecting x-rays inside the mouth, which can be conveniently moved inside the mouth, can increase user convenience, and has improved economic feasibility. The device for detecting x-rays inside the mouth according to the present invention comprises: a sensor unit having a sensor built therein for detecting x-rays; a hinge unit formed on one surface of the sensor unit; and a cable connecting unit including a pivoting connecting portion having an external cable coupled thereto and coupled to be pivotable to the hinge unit. An internal cable withdrawn from the sensor unit is electrically connected to the external cable through the inside of the cable connecting unit by means of the hinge unit and the pivoting connecting portion.

10 Claims, 8 Drawing Sheets

(56) References Cited

FOREIGN PATENT DOCUMENTS

| | | |
|---|---|---|
| JP | 2010-162326 A | 7/2010 |
| KR | 20-1998-0017858 U | 7/1998 |
| KR | 10-2009-0125366 A | 12/2009 |
| KR | 10-2013-0095498 A | 8/2013 |

* cited by examiner

INTRAORAL X-RAY DETECTOR

CROSS REFERENCE TO RELATED APPLICATIONS

This application is a National Stage Patent Application of PCT International Patent Application No. PCT/KR2014/012903 (filed on Dec. 26, 2014) under 35 U.S.C. § 371, which claims priority to Korean Patent Application Nos. 10-2013-0165339 (filed on Dec. 27, 2013), 10-2014-0169743 (filed on Dec. 1, 2014) and 10-2014-0169744 (filed on Dec. 1, 2014), the teachings of which are incorporated herein in their entireties by reference.

TECHNICAL FIELD

This invention relates to an intraoral X-ray detectors and to an intraoral X-ray detector which is freely movable and easily repairable because a cable connecting unit, to which an external cable is attached, is hinge-coupled to be rotatable, to be attachable and detachable to the sensor part.

BACKGROUND ART

In dentistry, generally, intraoral dental information is required to determine the conditions for the treatment of teeth, X-ray imaging device using the X-rays to obtain an intraoral dental information is provided.

The X-ray imaging device is comprised of an X-ray irradiator and the X-ray detector for detecting the irradiated X-rays, usually the X-ray irradiated from an outside of a mouth are detected by the X-ray detector inside the mouth.

As shown in FIG. 1, the conventional intraoral X-ray detector has a structure that a cable connecting unit 20 to which the external cable 30 is attached and a sensor unit 10 for detecting X-rays are formed integrally.

This conventional intraoral X-ray detector is not free to move the cable in the mouth, so there were drawbacks that an user should fold the cable to detect a particular tooth, or dispose the entire product even when the external cable connector are only damaged because the cable connecting unit and the sensor unit are formed in one body.

Furthermore, it should be done in the shortest path to retract the cable 30 from the mouth so that it can reduce the feeling of irritation of a patient. But as the conventional cable is fixed type, it can be different a folding degree of the cable or a retracting path of the cable as a position of teeth or a direction of biting. With these matters, the patient can be uncomfortable while obtaining images.

DETAILED DESCRIPTION OF THE INVENTION

Technical Problem

To solve the prior technical problem, this invention provides an intraoral X-ray detector which a sensor unit can be freely movable by a hinged connection between the sensor unit and a cable connecting unit which is connected to an external cable, and an external cable or a cable connecting unit can be easily replaceable when defects or damages are found in the external cable or the cable connecting unit.

Technical Solution

To achieve the object, the invention provides intraoral X-ray detector, including: a sensor unit having a built-in sensor for sensing X-rays; a hinge unit formed on one side of the sensor unit; a cable connecting unit being connected with an external cable and including a rotary coupling part rotatably coupling the cable connecting unit to the hinge unit, wherein an internal cable drawn from the sensor unit is electrically coupled to the external cable through the hinge unit, the rotary coupling part and inside of the cable connecting unit.

The cable connecting unit is coupled to the hinge in a detachable manner through the rotary coupling part, and the cable connecting unit further includes a cable connecting terminal configured to be connected to the external cable and separated from the external cable, electrically and physically.

The hinge unit may include a pair of hinges protruded facing each other in direction of a minor axis or the major axis direction on one side of the sensor unit, and a pair of hinge shafts protruded in a direction of facing each other from the pair of hinges, and the rotary coupling part includes a pair of connecting parts at both sides thereof, into which the pair of hinge shafts are respectively inserted.

The hinge unit may include a sunken shaped in a direction of a major axis or a minor axis on one side of the sensing unit and a pair of hinge shafts formed at both sides of the hinge unit, and the rotary coupling part includes a pair of connecting parts, at both sides thereof, into which the pair of the hinge shafts are respectively inserted.

The hinge unit may include a hinge formed in a sunken shape at one side of the sensor unit in the minor axis or the minor axis direction, and a pair of hinge shafts form at both sides of the hinge unit, and the rotary coupling part includes a pair of connecting parts, where the hinge shafts are respectively inserted, at both ends of the cable connecting unit.

The hinge unit is formed to be sloped in a major axis direction of the sensor unit, and the rotary coupling part rotatably couples the cable connecting unit to the hinge unit.

The hinge is formed on a corner at one side of the sensor unit. On the other hand, the hinge unit includes a pair of hinges facing each other and formed to be protruded from the sensor unit and a pair of hinge shafts formed on the hinges, and the rotary coupling unit includes a pair of connecting parts where the hinge shafts are inserted at both ends of the cable connecting unit.

Otherwise, the hinge unit may be connecting terminals which is connected to the sensor and is protruded from the both side of the sensor unit. The rotary coupling part has two ends which are rotatably assembled to the connecting terminal. And a terminal connecting electrode can be contained in the cable connecting unit. The terminal connecting electrode electrically connects the connecting terminal and the external cable.

Then, a first connecting hole and a second connecting hole are formed at both sides of the rotary coupling part to be connected to the connecting terminal. The connecting terminal is inserted through the first connecting hole and the second connecting hole and rotatably and electrically connected to the terminal connecting electrode.

Desirably, a stopper formed on one side of the cable connecting unit and configured to limit the rotating angle of the sensing unit.

Advantageous Effects

According to the present invention, the cable connecting unit being connected to the external cable can be rotatably attached to the sensor unit by the hinge unit for the sensor unit to be easily moved in a mouth and then the user convenience can be increased.

In addition, the cable connecting unit is detachably mounted on the hinge unit. The cable connecting unit further includes a cable connecting terminal which is electrically and physically connected to or separated with an external cable. Thus each component of the intraoral X-ray detector can be respectively replaced when there is a failure, and it is possible to have an effect of improving the economical efficiency and increasing of lifetime.

In addition, even if the rotary coupling part rotates, the electrical connection can be ensured. So it is possible to improve the reliability of performance.

NUMERALS STANDS FOR

Figure 1:
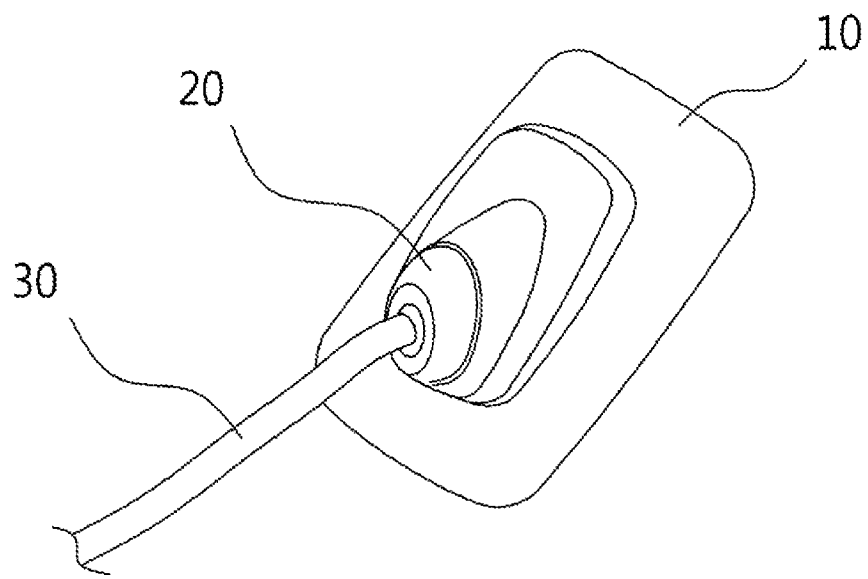
FIG. 1 is a prospective view schematically showing a conventional X-ray detector.

100: Sensor unit 310: First frame
110: Sensor 320: Second frame
200: Hinge 330: First connecting part
210: First hinge 340: Second connecting part
220: Second hinge 350: Cable connecting terminal
230: First hinge shaft 400, 1230: External cable
240: Second hinge shaft 500: Internal cable
300, 1200: Cable connecting unit 1120: Connecting terminal
1210: Upper housing 1220: Lower housing
1222: Connecting groove 1224: Second connecting hole
1226: Second connecting hole 1232: Cable accessing part
1240: Terminal connecting electrode 1242: First connecting hole
1122a, 1122b, 1122c: Terminal electrode
1242a, 1242b, 1242c: Exposed electrode part
1246a, 1246b, 1246c: Electrode
Best Mode for Carrying Out the Invention Hereinafter be described with reference to the accompanying drawings, preferred embodiments of the present invention. Embodiment of the present invention may be modified in various other forms of, but is not limited to the scope of the invention embodiment to be described below. Shape, size, etc. of the elements in the FIG.s may be exaggerated for more clear explanation, the elements represented by the same reference numerals on the drawings are the same element.

And in full herein, also it includes a case when some portion to said another portion and a "connection" which is not only the case, "directly connected to" another element in between "electrical connection" is that. In addition, when a part that is to some components "include" or "comprising", which means that not to exclude other components do not have a special substrate that is opposite to the other components may include or have the more.

In this embodiment, the "major axis" direction of the sensor unit denotes the direction toward the longer side of the sensor unit, and the "minor axis" direction of the sensor unit denotes the direction toward the shorter side of the sensor unit.

Figure 2:
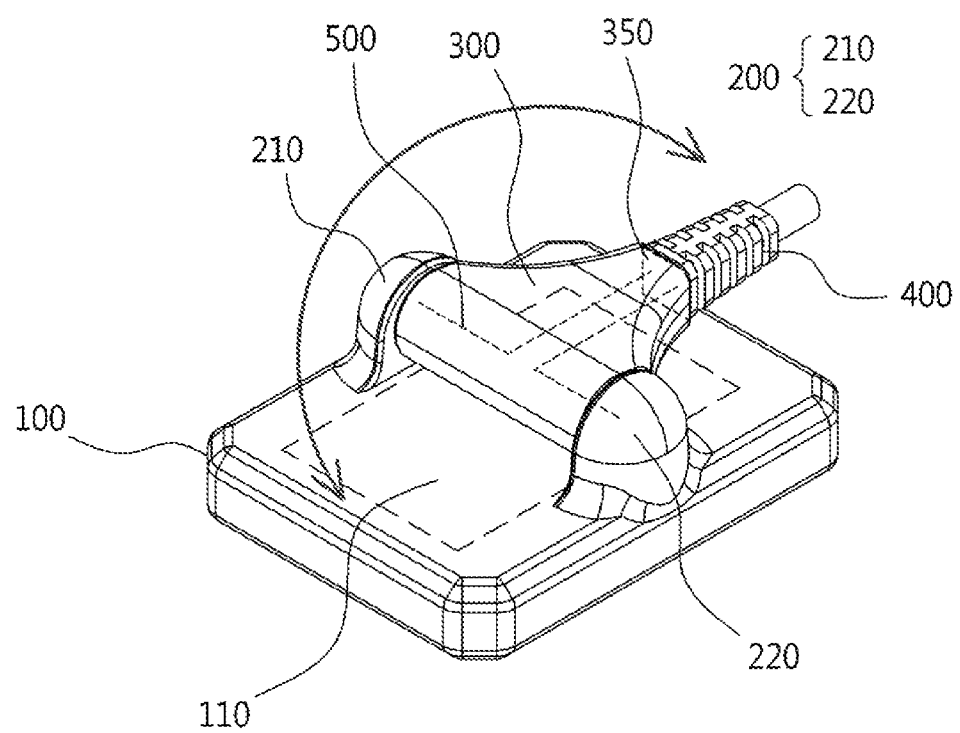
FIG. 2 is a perspective view showing the intraoral X-ray detector according to the first embodiment of the present invention.
Figure 3:
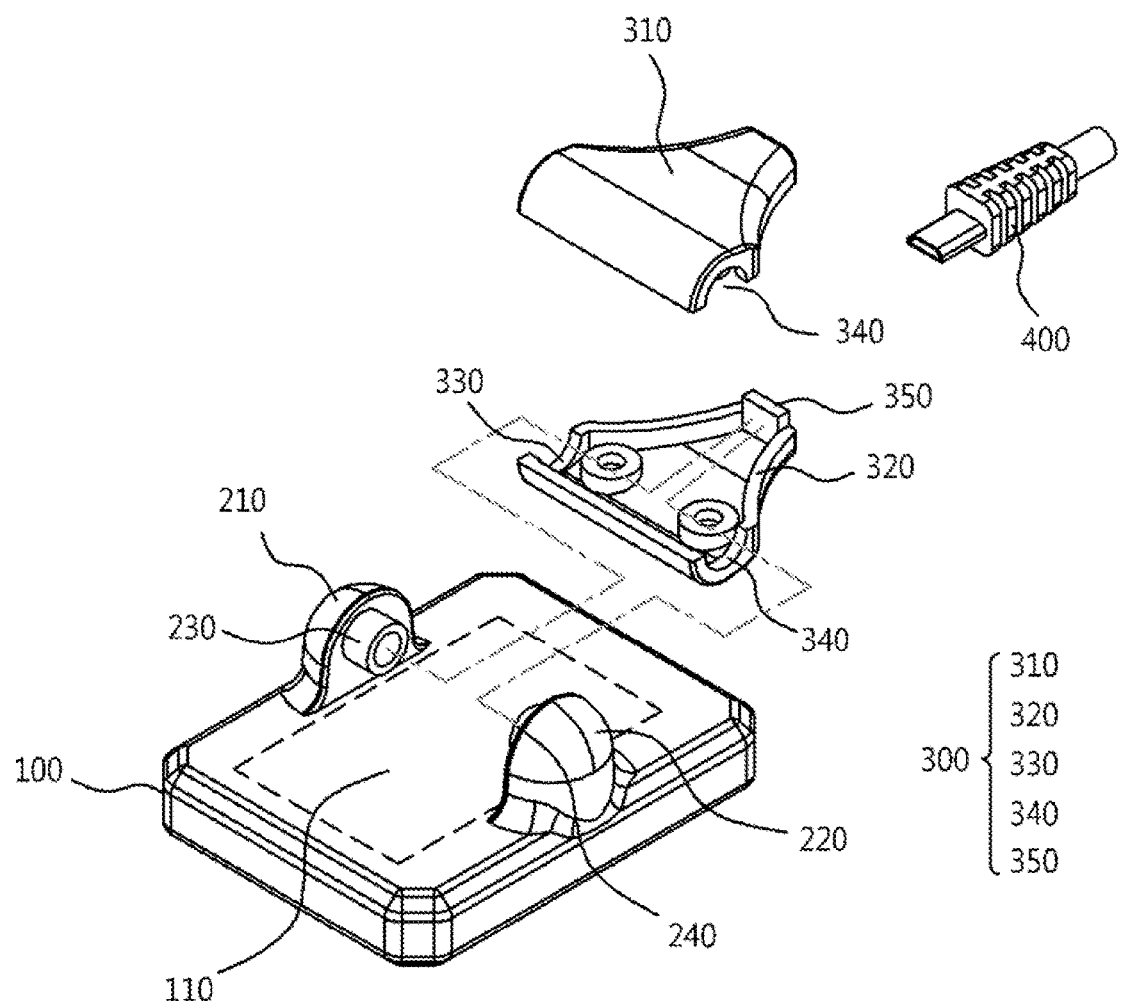
FIG. 3 shows a perspective view of the disassembled intraoral X-ray detector in FIG. 2.

FIGS. 2 and 3 are a perspective view and a disassembled perspective view of the first embodiment configuration of the present invention.

Referring to FIG. 2, the intraoral X-ray detector, according to an embodiment of the present invention, includes a sensor unit 100, a hinge unit 200, and a cable connecting unit 300.

In the sensor unit 100, a sensor 110 for detecting X-rays irradiated from an X-ray irradiation apparatus (not illustrated) is included, and a receiving surface of the sensor 110 faces toward a lower surface of the sensor unit 100. The sensor 110 may be a digital X-ray sensor and function of converting radiation signals into electric signals or image signals.

The digital X-ray sensor may be an indirect conversion type which converts radiation into visible light and converts again the visible light into electric signals, or a direct conversion type which converts the radiation directly into the electric signals.

The indirect conversion type may include a scintillator for converting radiation into visible light and a digital image sensor for detecting the visible light The direct conversion type has an assembled form of a photoconductive conversion unit for converting the radiation into the electric signals with use of semiconductor material and a signal processing unit for converting the electric signals into the image signals. And this enables to get high performance and high resolution because the radiations are converted directly into the electric signals.

The hinge unit 200 may be formed with two hinges, i.e., a first hinge 210 and a second hinge 220, and the first hinge 210 and the second hinge 220 are positioned to face each other. It is enough to locate the first hinge 210 and the second hinge 220 so as to face each other, at any side of the sensor unit 100 except the lower surface. Namely, the position of the hinge unit 200 is not limited to the upper surface different from the drawing.

A fixing pin (not illustrated) for fixing the rotation position of the cable connecting unit 300 may be included at the first hinge 210 or the second hinge 220. It is possible to enhance the convenience in use at various regions within the mouth by fixing the cable connecting unit 300 before the rotation or after the rotation in direction of arrow by use of the fixing pin.

That is, the rotation is possible by the hinge unit, it is possible to minimize the volume occupied by the cable because the structure enables the cable connecting unit 300 stick to the surface of the sensor unit 100. Thus, the patient can minimize the feeling of irritation.

The cable connecting unit 300 is rotatably connected to the first hinge 210 and the second hinge 220 and is able to move in the direction of the arrow. Further, an internal cable 500 drawn from the sensor 110 is connected, through the first hinge 210 and/or the second hinge 220 and through the inside of the cable connecting unit 300, to a cable connecting terminal 350 provided at one side of the cable connecting unit 300. In consequence, it is possible to transmit the electrical signals detected by the sensor 110 to an external cable 400.

Referring to FIG. 3, elements of intraoral X-ray detector in accordance with an embodiment of the present invention will be described in detail.

The first hinge 210 and the second hinge 220, for an example, may be formed by protrusion on the upper surface of the sensor unit 100 to have a cross-sectional surface of an oval shape in a vertical direction. The shape of the hinge is not limited to the oval shape but it may be modified in various shapes including a square, a rectangular and so on.

A first hinge shaft 230 is formed in a protrusion manner to have a circular cross-sectional shape in a vertical direction at one side of the first hinge 210. A second hinge shaft 240 is formed to have a corresponding shape to the first hinge shaft 230 at one side of the second hinge 220 which facing the one side of the first hinge 210. Only, the shape of the hinge shafts is not limited to the circular cross-sectional shape, but it can be variously modified as like hexagonal or octagonal shape.

According to one embodiment of the invention, a first hinge shaft 230 and a second hinge shaft 240 are separated each other for easy attachment and detachment with the cable connecting unit 300 to be described later. However, they are not limited to this, but the first hinge shaft 230 and the second hinge shaft 240 may be linked to have one hinge shaft.

The cable connecting unit 300 may be formed with a first frame 310 and a second frame 320 separable so as to be combined in attachable and detachable form to the hinge unit 200. In specific, a first connecting part 330 and a second connecting part 340 are formed to face each other at one portion of a side surface of the cable connecting unit 300 where the first frame 310 and the second frame 320 are coupled, the first connecting part 330 is coupled to the first hinge shaft 230 and the second connecting part 340 is coupled to the second hinge shaft 240 so that the cable connecting unit 300 is combined in a attachable and detachable with the hinge unit 200.

The first connecting part 330 and the second connecting part 340 are combined to wrap first hinge shaft 230 and the second hinge shaft 240 respectively. For this, the first connecting part 330 and the second connecting part 330 may be respectively formed in a shape of a circle corresponding to a cross-sectional surface in a vertical direction of the first hinge shaft 230 and the second hinge shaft 240. Additionally, not limited to this, it can be changed according the cross-sectional shape of the first hinge shaft 230 and the second hinge shaft 240 in a vertical direction.

In the embodiment of the present invention, the first hinge shaft 230 and the second hinge shaft 240 are respectively formed in the first hinge 210 and the second hinge, and the first connecting part 330 and the second connecting part 340 are respectively formed in the cable connecting unit 300 to have a hinge coupling each other. However, on the contrary, it is also possible that the first hinge shaft 230 and the second hinge shaft 240 are respectively formed in the cable connecting unit 300, and the first connecting part 330 and the second connecting part 340 are respectively formed on the first hinge 210 and the second hinge 220 have a hinge coupling each other. Besides, the sensor unit 100 and the cable connecting unit 300 may have the hinge coupling by changing the position of the hinge shaft and the hinge pin in variety.

A cable connecting terminal 350 to be physically and electrically connected to or separated from the external cable 400 is formed at the rear side of the cable connecting unit 300, and the electric connection is possible by inserting a connecting terminal of the external cable into the cable connecting terminal 350. The internal cable 500 drawn from the sensor 110 of the sensor unit 100 is coupled to the cable connecting terminal 350 in side of the cable connecting unit 300 through the first hinge 210 and/or the second hinge 220 of the sensor unit 100 and the first connecting unit 330 and/or the second connecting unit 340 of the cable connecting unit 300. Thus, the external cable 400 is electrically coupled to the sensor 110 of the sensor when the connecting terminal of the external cable 400 is inserted into the cable connecting terminal 350. By doing this, the electric signals detected by the sensor 100 can be delivered to the external table 400.

In the embodiment of the present invention, the external cable 400 and the cable connecting terminal 350 are respectively formed of a micro USB cable and a micro USB connecting terminal, but not limited there to, and various modifications including USB cable may be adopted.

In the embodiment of the present invention, the cable connecting unit and the external cable can be detachably combined through the cable connecting terminal, but not limited there to, and the cable connecting unit and the external cable can be modified in an integral form in consideration of usage environment.

Desirably, the internal cable 500 and the external cable 400 are connected by a jumper cable (not illustrated) inside the cable connecting unit 300, or it is possible to make the external and internal cables are electrically coupled when hinge coupling of the first hinge shaft 230 and/or the second hinge shaft 240 and the first connecting unit 330 and/or the second connecting unit 340 by forming a first contacting terminal (not illustrated) to which the internal cable 500 is connected is formed at the first hinge 230 and/or the second hinge 240.

In particular, in case of the latter, the electrical connection can be maintained in stable despite of the rotation of the cable connecting unit 300 about the sensor unit 100 if slip rings and brushes are used as the first contacting terminal (not illustrated) and the second contacting terminal (not illustrated)

The sensor unit 100 may be formed in a rectangular shape so as to take images in a direction of the normal teeth array and installed horizontally on the sensor unit. In the above embodiment, the first and second hinges 210 and 220 and the first and second hinge shafts 230 and 240 are disposed in a minor axis direction of the sensor unit. However, this hinge structure can be varied depending on the use or orientation of the sensor.

FIGS. 4 to 9 are related to several embodiments of modification of the structure of the hinge combination between the cable connecting units 302 to 307 and the sensor units 102 to 107.

Figure 4:
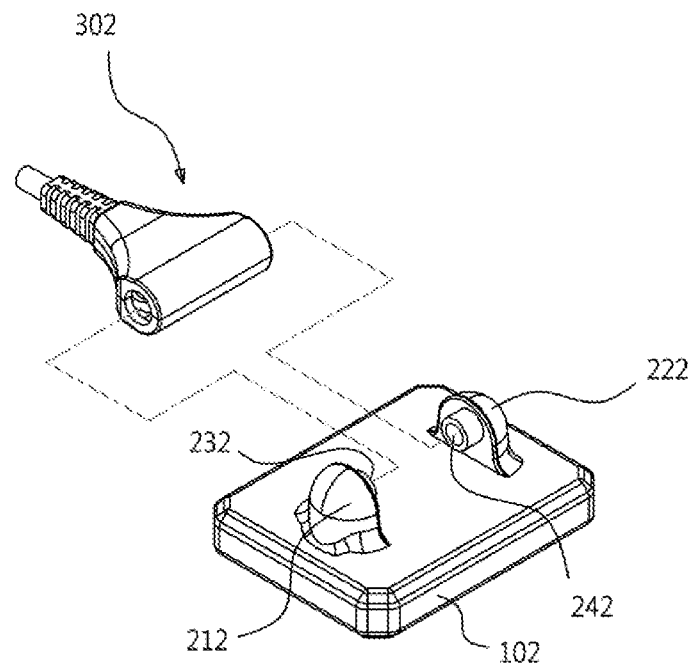
FIGS. 4 to 9 are views showing components of intraoral X-ray detector according to various modifications of the first embodiment of the present invention.

FIG. 4 is a disassembled perspective view showing another modified embodiment of the invention in FIG. 3

In this embodiment, since the cable connecting unit 302 has the same configuration as the embodiment in FIG. 3, detailed description thereof will be omitted. In the sensor unit 102, a first hinge 212 and a second hinge 222 facing each other in the major axis direction are formed in the sensor unit 102, the first hinge shaft 232 is formed in the first hinge 212, and the second hinge shaft 242 is formed in the second hinge 222. In this case, it is useful to minimize the feeling of irritation due to the cable when imaging is performed in the longitudinal direction to cover the root of the particular tooth by use of the sensor unit 210.

Figure 5:
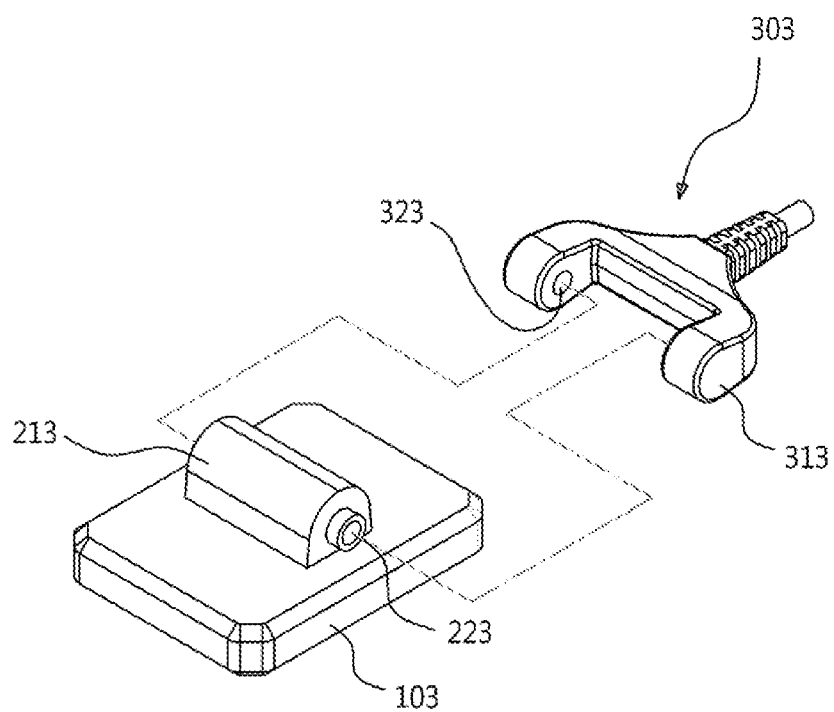

FIG. 5 is a disassembled perspective view showing another modified embodiment of the invention in FIG. 3.

In this embodiment in FIG. 5, the sensor unit 103 includes a hinge unit 213 which is formed protruding in the minor axis direction and a hinge shaft 223 formed at both side surfaces of the hinge unit, a cable connecting unit 303 is divided into two branches to have a rotary coupling part, which includes a first connecting part 313 to which the first hinge shaft 213 is inserted and the second connecting part 323 to which the second hinge shaft 213 is inserted are provided at inner side of the two divided ends. Accordingly, the cable connecting unit 303 is pivotally coupled and connected at both ends of the hinge unit 213.

Figure 6:
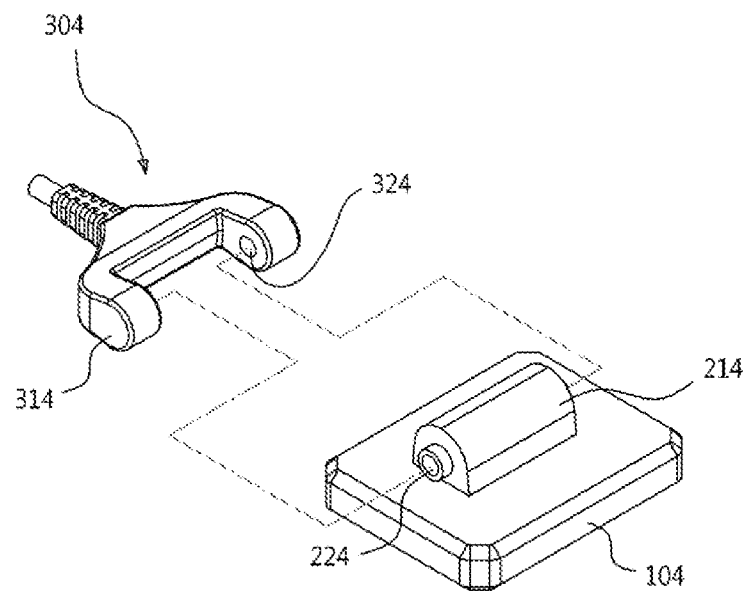

FIG. 6 is an exploded perspective view showing the X-ray detector according to a fourth embodiment of the present invention.

In this embodiment, the sensor unit 104 includes a hinge 214 protrude in the major axis direction and a hinge shaft 224 formed at both side surfaces of the hinge. Like as the third embodiment, the cable connecting unit 304 includes a first connection unit 314 and a second connecting unit 324. Accordingly, the cable connecting unit 304 is pivotally coupled and connected at both ends of the hinge 214.

Figure 7:
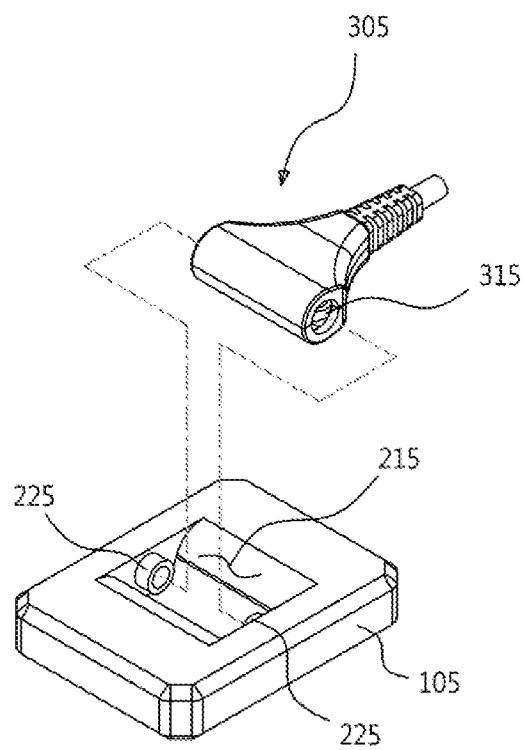

FIG. 7 is an exploded perspective view showing another modified embodiment of the invention in FIG. 3.

In this embodiment in FIG. 7, the sensor unit 105 includes a hinge unit 215 having a sunken shape in the minor axis direction and a pair of hinge shafts 225 protruded toward inside at both side surfaces of the hinge. Like as the first and the second embodiments, the cable connecting unit 305 includes a pair of connecting units 315 to which a pair of hinges 225 are inserted at both ends thereof. Accordingly, the cable connecting unit 305 is pivotally coupled and connected at the hinge 215 inside of the sensor 105.

Figure 8:
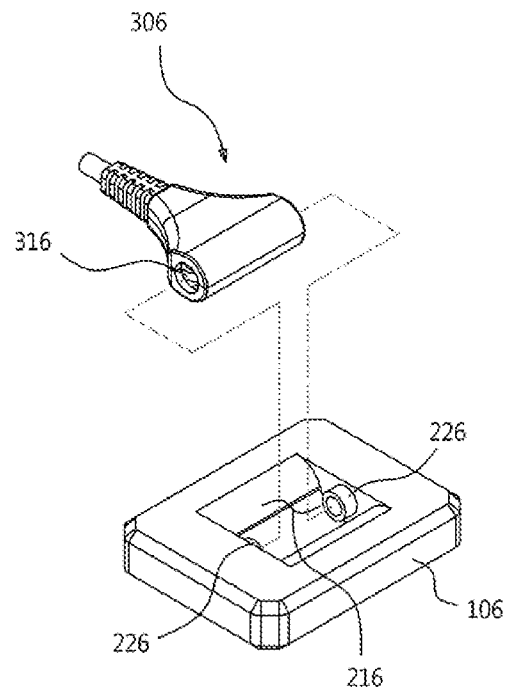

FIG. 8 is an exploded perspective view showing another modified embodiment of the invention in FIG. 3.

This embodiment has modified a rotational direction of the embodiment, in FIG. 7, the sensor unit 106 includes a hinge unit 216 formed as a sunken shape in the major axis direction and a pair of hinge shafts 226 formed inwardly at both side surfaces of the hinge unit 216. Like as the fifth embodiment, the cable connecting unit 306 includes a pair of connecting units 326. Accordingly, the cable connecting unit 306 is pivotally coupled at the hinge 216 inside of the sensor 106.

Figure 9:
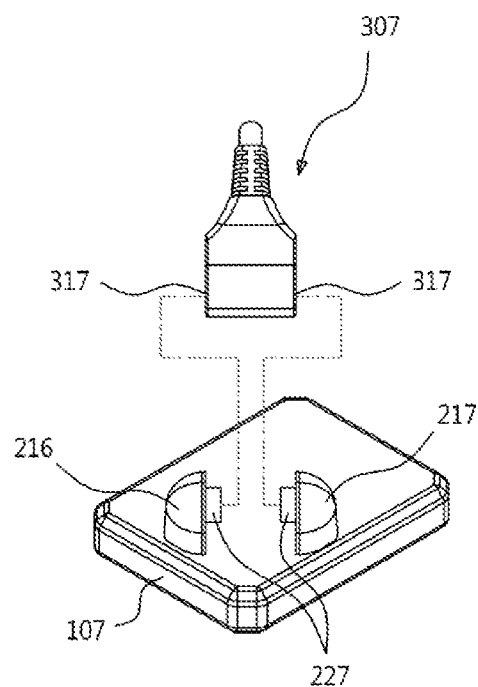

FIG. 9 is a view showing another modified embodiment of the invention in FIG. 3.

The sensor unit 107 includes a pair of hinge units 217 facing each other in a direction sloped by a predetermined angel about the major and the minor axes direction and protruded from the sensor unit 107 and a pair of hinge shafts formed on the hinge, and a cable connecting unit 307 includes a pair of connecting units 317 at both ends there of the hinge shafts 227 are inserted. In this case, it has advantage of minimizing the size of the cable connecting unit 307 because it is possible to form the hinges 217 at the corners of the sensor unit 107.

By the modification the embodiment in FIG. 9, it is possible to combine the cable connecting unit at both sides of the hinge or to form hinge units in a sunken shape.

In the embodiments in FIG. 3 to FIG. 9, the sunken shape or the protrusion of the hinges is applicable with a modification, and all the structures with which the hinge shaft and the connecting unit are to be pivotally coupled each other are within the present invention. For an instance, although it has not been described in the embodiments above, a rotational axis is formed on the cable connecting unit, and a connecting part of concave type may be formed on the hinge. In other words, the hinge and the connecting part may be substitute with hinges coupling each other and rotational connecting part corresponding thereto.

Figure 10:
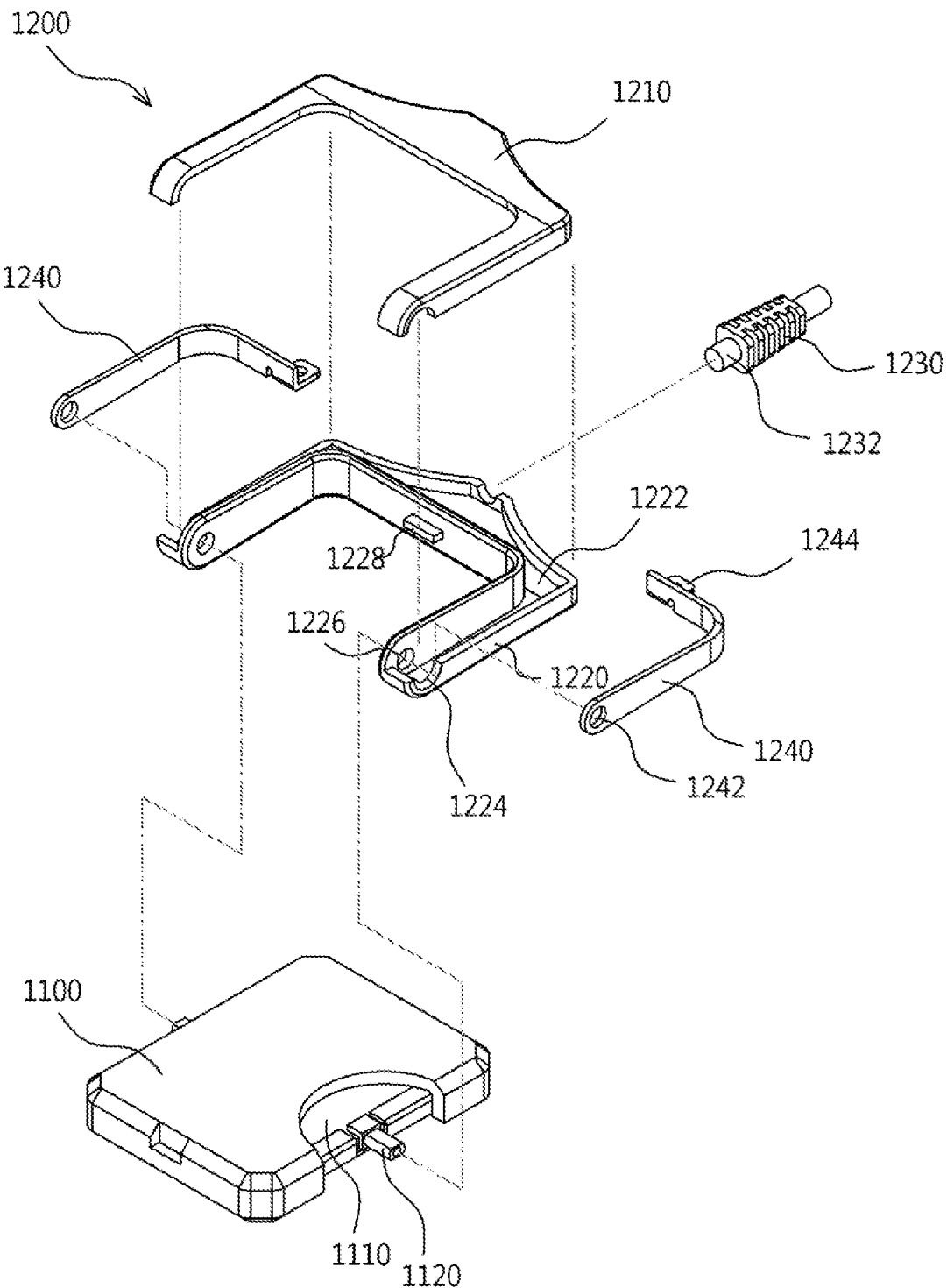
FIG. 10 is a perspective view showing the disassembled intraoral X-ray detector according to the second embodiment of the present invention.
Figure 11:
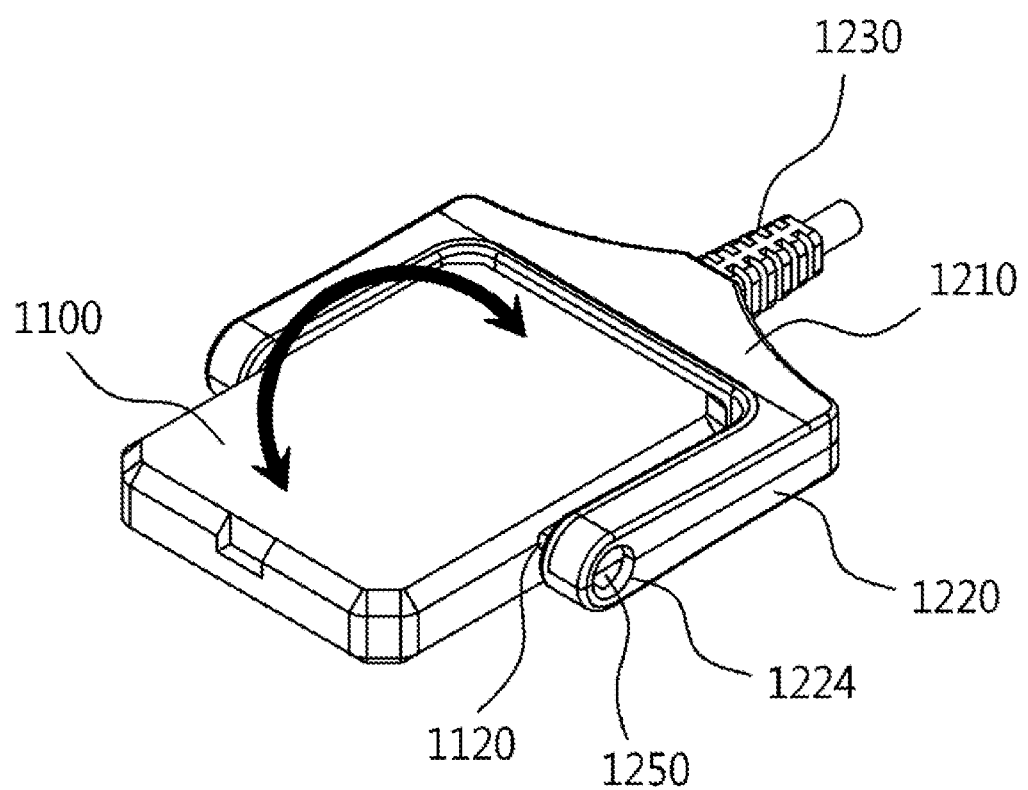
FIG. 11 shows a perspective view of the assembled intraoral X-ray detector in FIG. 2.

FIGS. 10 and 11 are a perspective view and an exploded perspective view of a second embodiment configuration of the present invention.

As shown in FIG. 10, the intraoral X-ray detector according to an embodiment of the present invention, includes a sensor unit 1100, a cable connecting unit 1200, and an external cable 1230.

The sensor 1110 is equipped with in the sensor unit 1100, and a pair of connecting terminals 1120 in the sensor unit which is electrically connected with the sensor are exposed at both sides of the sensor unit. For reference, in FIG. 10, a part of the sensor unit is illustrated in cutting view in order to show the sensor and sensor unit connecting terminal 120 therein. The rotary coupling part 200 is branched in "U" shape so that both end parts are pivotally and electrically connected to the connecting terminal 120.

A cable connecting unit 1200 includes an upper housing 1210 and a lower housing 1220, and further includes a connecting groove 1222 formed with one of these or combination thereof. In the connecting groove, a terminal connecting electrode 1240 which is made of the conductive material for delivering the power source and/or the signal is inserted. The electrode is formed in the u-shaped and is connected to the connecting terminal 1120 in both ends of a rotary coupling part of the sensor unit 100, and is connected to the external cable 1230. In the present preferred embodiment, it is classified with the two for the convenience of assembly, the terminal connecting electrode 1240 is formed in a divided two parts for an easy assemble, and each segment is connected to the one of the terminal connecting electrode, and they are respectively connected to the external cable 1230. The external cable 1230 is inserted and coupled together when the upper and lower housings 1210 and 1220 are assembled. And the cable accessing part 1232 which is an end part of the external cable 1230 is connected to the joint part 1244 of the terminal connecting electrode 1240. At this time, if necessary, the external cable 1230 may be connected to the terminal connecting electrode 1240 through the joint part 1244 by inserting the cable accessing part 1232 of the external cable 1230 at a side of an assembled body of the lower and the upper housings 1210 and 1220.

At the end of the electrode 1240, a first connecting hole 1242 is formed, and a second connecting hole 1226 is also formed in the corresponding position in the end of the lower housing 1220. The connecting terminal 1120 as a hinge shaft is rotatably and electrically connected to the terminal connecting electrode 1240 through the second connecting hole 1226 by being inserted into the first connecting hole 1242. Therefore, the sensor 1110 within the mouth is electrically connected to the cable connecting unit 1230 connected to the outside.

In order that the sensor unit 100 sets up the initial position of the sensor, it is desirable not to rotate over 180°. A protruded stopper 1228 is formed at one side of the cable connecting unit 1200, and the seating groove 1102 contacting with the stopper when the sensor unit 100 rotated with 180° is formed in the sensor unit 1100.

As shown in FIG. 11, if the sensor unit 1100, the cable connecting unit 1200 and external cable 1230 are assembled, the sensor unit 1100 can be rotated according to the arrow, and it is limited by the stopper 228 in which the rotation range describes in the above with ±180°. In this preferred embodiment, a third connecting hole 1224 is formed when the upper and lower housings 1210 and 1220 of the cable connecting unit 1200 are assemble, and it is sealed up with the insulator 1250. Through this, it can be easily assembled, and the liquid within the mouth is electrically separated from the internal terminal 1120 and the terminal connecting electrode 1240.

In this preferred embodiment, a electrical power is supplied through the cable connecting unit 1230, terminal connecting electrode 1240, and connecting terminal 1120 since the connecting terminal 1120 and the first connecting hole 1242 of the terminal connecting electrode 1240 rotate relatively, and it is possible to configure so that the sensing signal of the sensor unit 1100 can be transmitted and received wirelessly through the communication unit which is not illustrated and mounted within the sensor unit 1100. On the other hand, the electrical power is supplied through the external cable 1230 and the terminal connecting electrode 1240, and it is possible to deliver the electric signals generated by the intraoral X-ray imaging in the sensor 1110 of the sensor unit 1100 to the outside through the connecting terminal 1120, the terminal connecting electrode and the external cable 1230.

Figure 12:
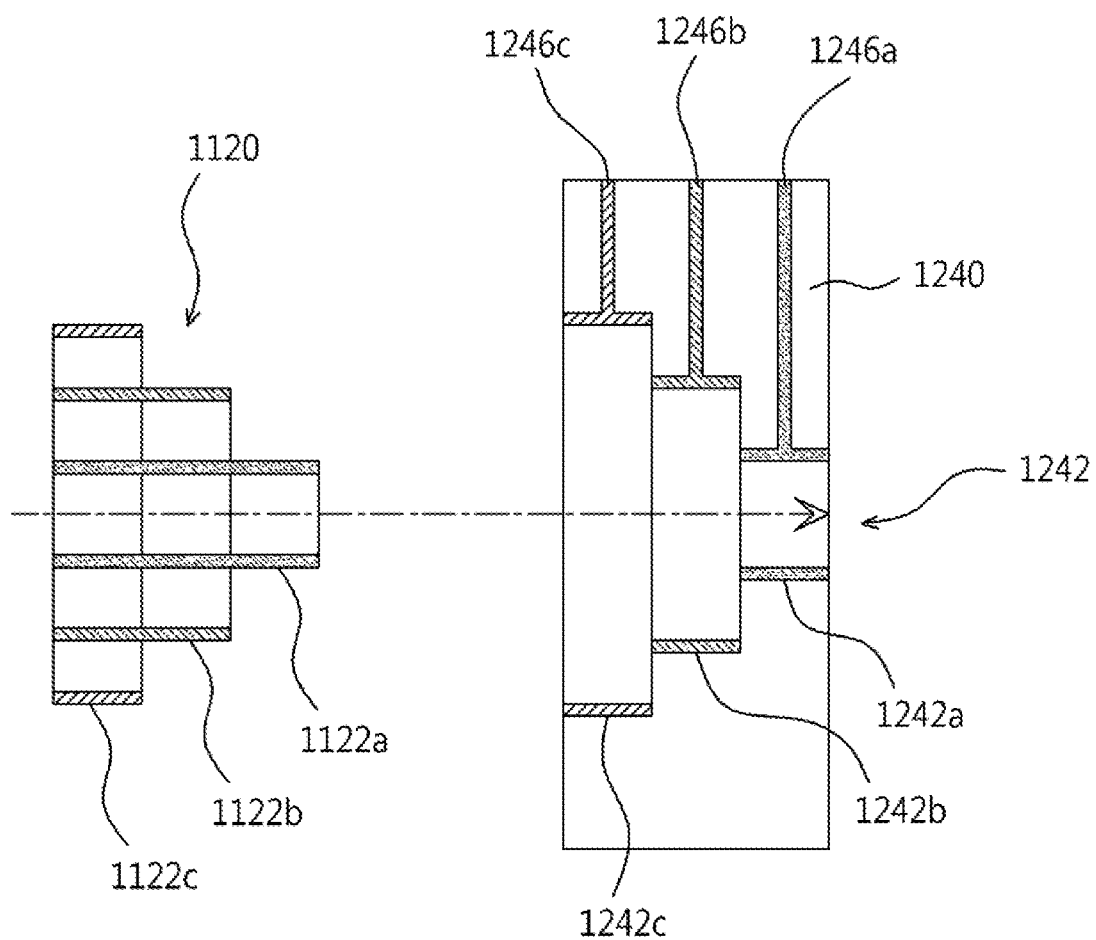
FIG. 12 is a sectional view showing a connecting structure of the connecting terminal and the terminal connecting electrode of the X-ray detector in FIG. 10.

FIG. 12 shows the section structure of the modified connecting terminal 1120 and the first connecting hole 1242 of the terminal connecting electrode 1240 in the oral X-ray detector according to the present invention. As described in FIG. 12, the connecting terminal 1120 has three electrodes 1122a, 1122b, 1122c composed of the concentric circle, and each electrode is formed to be stepped and is exposed to the outside and insulated each other. In the meantime, the first connecting hole 1242 of the terminal connecting electrode is formed to be stepped and has three internally exposed electrodes 1246a, 1246b, 1246c which are electrically insulated in each other. It is desirable that the remaining part of the electrode for the terminal connection is made of the insulating material since the three electrodes should be electrically isolated. Instead of wholly forming the terminal connection electrode 1240 with conductive material, it may have the form of PCB having multiple conductive lines on an insulator. If the connecting terminal 1120 is inserted into the first connecting hole 1242, only the electrodes of corresponding electrodes are contact to each other, in that way, electrodes of the respective connecting terminal 1120 are independently connected to the corresponding electrodes of the electrode 240 for the terminal connection.

Exposed parts 1242a, 1242b, 1242c inside of the first connecting hole 1242 of each of the terminal connecting electrode 1240 are made of the ring or the brush form, and the contact with the electrodes of the connecting terminal 1120 are authentically maintained although the connecting terminal 1120 rotates. Moreover, the exposed part is conductive and has bearing form so that it can facilitate the rotation easily.

Or on the other hand, the connecting terminal 1120 and the first connecting hole 1242 of the terminal connecting electrode 1240 can be electrically connected in a multiple slip ring structure including multiple slipping electrodes insulated each other instead of a correspondingly stepped form at connecting terminal 1120, multiple brush electrodes faced and contacted in one-to-one to the multiple slipping electrodes at the first connecting hole 1242 of the terminal connecting electrode 1240.

In the above preferred embodiment, the three electrodes are used for power, signal transmission and signal reception. However, the number of electrode can be changed according to the driving method of the oral device for taking x-ray photographs, the imaging mechanism or software used.

Consequently, according to the posture of the sensor unit 1100, it rotates at the angle in which the patient minimally can do the feeling of irritation of cable during the oral X-ray imaging because the cable connecting unit 1200 can rotate and the inconvenience of the patient can be minimized.

Moreover, the cable connecting unit 1200 rotates about the sensor unit 1100. And yet the circuit line in which the electrical connection can be authentically maintained is formed. Therefore, the transmission and/or reception including the power source or the image signal etc. can be guaranteed.

The invention described above is not limited to the above-described embodiments and drawings, It will be apparent to a person with a number of substituted, conventional knowledge in the art to which the invention pertains that variations and modifications are possible without departing from the scope of the technical concept of the present invention.

The invention claimed is:

1. An intraoral X-ray detector comprising:
 a sensor configured to detect X-rays within a mouth;
 a sensor unit configured to have the sensor;
 a hinge unit including a connecting terminal as a hinge shaft configured to electrically connect to the sensor; and,
 a cable connecting unit configured to be connected to an external cable and rotatably attached to the hinge unit,
 wherein the hinge unit further includes a pair of hinges protruded facing each other in a direction of a major axis or a minor axis on one side of the sensor unit and a pair of hinge shafts protruded in a direction of facing each other from the pair of hinges, and the cable connecting unit includes a pair of connecting parts in which the pair of hinge shafts is inserted.

2. The intraoral X-ray detector of claim 1, wherein the cable connecting unit includes a terminal connecting electrode configured to connect the connecting terminal and the external cable.

3. The intraoral X-ray detector of claim 1, wherein the cable connecting unit further includes a cable accessing part configured to be connected to the external cable and separated from the external cable, electrically and physically.

4. The intraoral X-ray detector of claim 1, wherein the hinge unit further includes a hinge protruded in a direction of a major axis or a minor axis on one side of the sensor unit and a pair of hinge shafts formed at both sides of the hinge unit, and
 the cable connecting unit include a pair of connecting parts, at both sides thereof, into which the pair of hinge shafts are respectively inserted.

5. The intraoral X-ray detector of claim 1, wherein the hinge unit includes a sunken shaped hinge in a direction of a major axis or a minor axis on one side of the sensor unit and a pair of hinge shafts formed at both sides of the hinge unit, and
 the cable connecting unit include a pair of connecting parts, at both sides thereof, into which the pair of hinge shafts are respectively inserted.

6. The intraoral X-ray detector of claim 1, wherein the hinge unit is formed to be sloped in a major axis direction of the sensor unit on one side of the sensor unit, and
 the cable connecting unit is removably attached to the hinge unit.

7. The intraoral X-ray detector of claim 1, wherein the connecting terminal is protruded in both directions of the sensor unit, and both sides of the cable connecting unit are separately divided to be rotatably attached to the connecting terminal.

8. The intraoral X-ray detector of claim 7, wherein a first connecting hole and a second connecting hole are formed at both sides of the cable connecting unit to be connected to the connecting terminal, and
the connecting terminal is inserted through the first connecting hole and the second connecting hole and rotatably and electrically connected to a terminal connecting electrode.

9. The intraoral X-ray detector of claim 8, wherein the first connecting hole and the second connecting hole are concentric and different in size to become a stepped shape, and the connecting terminal has a corresponding shape.

10. The intraoral X-ray detector of claim 7, further comprising:
a stopper formed on one side of the cable connecting unit and configured to limit the rotating angle of the sensor unit.

* * * * *